United States Patent
Schwartz et al.

(10) Patent No.: US 12,053,608 B1
(45) Date of Patent: Aug. 6, 2024

(54) MICRO-NEEDLING ARRAY TREATMENT ASSEMBLY

(71) Applicant: ProCell Therapies, LLC, Austin, TX (US)

(72) Inventors: Mitchell Edward Schwartz, Clearwater, FL (US); Daniel Troyen-Schwartz, St. Petersburg, FL (US)

(73) Assignee: ProCell Therapies, LLC, Austin, TX (US)

( * ) Notice: Subject to any disclaimer, the term of this patent is extended or adjusted under 35 U.S.C. 154(b) by 0 days.

(21) Appl. No.: 18/197,935

(22) Filed: May 16, 2023

Related U.S. Application Data

(63) Continuation-in-part of application No. 29/884,654, filed on Feb. 14, 2023, and a continuation-in-part of application No. 29/884,664, filed on Feb. 14, 2023, and a continuation-in-part of application No. 29/884,655, filed on Feb. 14, 2023.

(51) Int. Cl.
    *A61M 37/00* (2006.01)
(52) U.S. Cl.
    CPC . *A61M 37/0015* (2013.01); *A61M 2037/0023* (2013.01); *A61M 2037/0061* (2013.01)
(58) Field of Classification Search
    CPC ...... A61M 37/0015; A61M 2037/0061; A61M 2037/0023
    See application file for complete search history.

(56) References Cited

U.S. PATENT DOCUMENTS

| | | |
|---|---|---|
| D268,812 S | 7/1983 | Lancellotti |
| 4,644,952 A | 2/1987 | Patipa et al. |
| 4,798,582 A | 1/1989 | Sarath et al. |
| 5,190,523 A | 3/1993 | Lindmayer |
| 5,279,552 A | 1/1994 | Magnet |
| D346,024 S | 4/1994 | Hood et al. |
| D351,022 S | 9/1994 | Saito |
| D358,082 S | 5/1995 | Trezza |
| D398,216 S | 9/1998 | Woodgate |
| D425,388 S | 5/2000 | Lin |
| D461,898 S | 8/2002 | Frye |
| D496,724 S | 9/2004 | Myers et al. |

(Continued)

FOREIGN PATENT DOCUMENTS

KR    3010981310003    3/2021

OTHER PUBLICATIONS

M. C. Aust, D. Fernandes, p. Kolokythas, H. M. Kaplan, P. M. Vogt, "Percutaneous Collagen Induction Therapy: An Alternative Treatment for Scars, Wrinkles, and Skin Laxity", Plastic Reconstructive Surgery, 2008, vol. 121, pp. 1421-1429.

(Continued)

*Primary Examiner* — Amber R Stiles
(74) *Attorney, Agent, or Firm* — Thomas G. Ference

(57) ABSTRACT

A micro-needling system, the system includes a micro-channeling device, a needle tip connector and a variety of micro-needling assemblies. The micro-channeling device is designed to provide reciprocal motion, in and out of skin, for the micro-needling assemblies when applied to skin. A quick connector is provided for easy interchange of the micro-needling assemblies. Benefits of the system include ergonomic holding, versatility of needle arrays and reduced vibration.

9 Claims, 18 Drawing Sheets

(56) References Cited

U.S. PATENT DOCUMENTS

| | | | |
|---|---|---|---|
| D497,509 S | 10/2004 | Nelson | |
| D526,411 S | 8/2006 | Easley | |
| D553,738 S | 10/2007 | Simonson | |
| D623,369 S | 9/2010 | Sugita et al. | |
| D630,733 S | 1/2011 | Ahlgren | |
| D676,958 S | 2/2013 | Doll et al. | |
| 8,414,531 B2 | 4/2013 | Oginski et al. | |
| D718,315 S | 11/2014 | Garner et al. | |
| D726,314 S | 4/2015 | Marquez | |
| D726,316 S | 4/2015 | Marquez | |
| D791,946 S | 7/2017 | Schwartz | |
| D854,148 S | 7/2019 | Prinz | |
| D868,855 S | 12/2019 | Spillane | |
| 10,596,011 B2 | 3/2020 | Beck et al. | |
| D882,732 S | 4/2020 | Hansen | |
| D893,028 S | 8/2020 | Schwartz | |
| D917,049 S | 4/2021 | Schwartz | |
| D925,030 S | 7/2021 | Hilton et al. | |
| D939,704 S | 12/2021 | Bales et al. | |
| D950,723 S | 5/2022 | Leibowitz | |
| D942,020 S | 6/2022 | De Klein et al. | |
| D972,726 S | 12/2022 | Spencer | |
| D980,976 S | 3/2023 | Virk et al. | |
| D987,823 S | 5/2023 | Rittierott et al. | |
| D991,767 S | 7/2023 | Urbanek | |
| 2003/0199811 A1* | 10/2003 | Sage, Jr. | A61B 17/54 606/186 |
| 2006/0142708 A1 | 6/2006 | Hazut et al. | |
| 2006/0253079 A1 | 11/2006 | McDonough et al. | |
| 2009/0036922 A1* | 2/2009 | Riskin | A61B 17/105 606/215 |
| 2009/0137945 A1 | 5/2009 | Marquez | |
| 2016/0082241 A1* | 3/2016 | Burton | A61M 37/0015 604/173 |
| 2016/0354590 A1* | 12/2016 | Lee | A61M 37/0015 |
| 2019/0125547 A1 | 5/2019 | Birkbeck et al. | |
| 2019/0366067 A1* | 12/2019 | Ginggen | A61B 17/32053 |
| 2020/0338287 A1 | 10/2020 | Chan et al. | |
| 2021/0228378 A1 | 7/2021 | Atkin et al. | |
| 2021/0316441 A1 | 10/2021 | Ting Ya | |

OTHER PUBLICATIONS

H. Liebl, L. C. Kloth, "Skin Cell Proliferation Stimulated by Microneedles", Jouimal of the Amerian Colege of Clinical Wound Specialists, 2023, vol. 4, pp. 2-6.

A. Camirand, J. Doucet, "Needle Dermabrasion", Aesthetic Plastic Surgery, Jan.-Feb. 21, 1997, (1), pp. 48-51.

D. Fernandes, "Minimally Invasive Percutaneous Collagen Induction", Oral and Maxillofacial Surgery Clinics of North America, Feb. 1, 2005, (1), pp. 51-63.

L. F. Jaffe, J. W. Vanable Jr., "Electric Fields and Wound Healing", Clinics in Dermatology, 1984, vol. 2, Issue 3, Jul.-Sep., pp. 34-44.

D. S. Orentreich, N. Orentreich, "Subcutaneous Incisionsless (Subcision) Surgery for the Correction of Depressed Scars and Wrinkles", Dermatol Surgery, Jun. 21, 1995, pp. 543-549.

Printed May 1, 2023, "Dr. Pen—USA—Microneedling Pen", https://drgpen-usa.com/?gclid=EAlalQobChMI-rnh68Dw_glVpcfjBx3p7ge2DAMYASAAEgLsw_D-BwE. 3 pages.

Procell Microchanneling Faqs, procellmicrochannelingtraining.com, [online], [site visited Aug. 2, 2023], Available from Internet URL: https://www.procellmicrochannelingtraining.com/procell-microchanneling-training-faqs-s/101.htm (Year: 2023).

Surface Microchanneling Treatment, switch2pure.com, [online], [site visited Aug. 2, 2023], Available from Internet, URL: https://switch2pure.com/surface-microchanneling-treatment/?sku=22544113 (Year: 2023).

TheraFace PRO Hot and Cold Rings, amazon.com, customer reviews oldest Apr. 19, 2022 [online], [site visited date Mar. 9, 2023], Available from the Internet, URL: https://www.amazon.com/TheraFace-Attachments-Tension-Inflamation-Therabody/dp/B09TZ2PVK5 (Year:2022).

Facial Cleansing Brush Face Scrubber: COSLUS, amazon.com, first available Jul. 29, 2021 [online], [site visited date Aug. 9, 2023], Available from Ineternet, URL: https://www.amazon.com/Facial-Cleansing-Brush-Face-Scrubber/dp/B09KNNN535 (Year: 2021).

Screen captures from YouTube video clip entitled "ProCell Microchanneling Training Video", uploaded on Nov. 29, 2021 by user "Mountain Coast Distributors, Inc.", Retrieved from Internet <https://www.youtube.com/watch?v=xYwAW1PU3S0> (Year: 2021).

Screen captures from YouTube video clip entitled "ProCell Microchanneling in 2 Minutes", uploaded on Nov. 29, 2021 by user "Mountain Coast Distributors, Inc.", Retrieved from Internet <https://www.youtube.com/watch?v=cvK4uMixrbA> (Year: 2021).

Stem cell snake oil for sale at Nordstrom, Amazon, and & Ebay?, [online], ipscell.com, Feb. 7, 2016 [retrieved on Mar. 2, 2023], Retrieved from the Internet <https://ipscell.com/2016/02/stem-cell-snake-oil-for-sale-at-nordstrom-amazon-ebay/> (Year: 2016).

Procell Microchannelling machine illustration, etsy.com, customer reviews oldest date May 20, 2023 [online], [site visited Aug. 2, 2023], Available from Internet, URL: https://etsy.com/listing/1419464024/procell-microchanneling-machine (Year:2023).

Procell Therapies launches the Next Generation of Microchanneling Device, [online], procelltherapies.com, Aug. 12, 2022 [retrieved on Aug. 2, 2023], Retrieved from the Internet <https://www.procelltherapies.com/blog/3/procell-therapies-launches-the-next-generation-of-microchanneling-device-14> (Year: 2022).

Sku Procell Pro, Procell Treatment, medpurchasing.com, [Post date: Feb. 3, 2023], [Site seen Jul. 25, 2023], Seen at URL: https://medpurchasing.com/product/procell-therapies-microchanneling-device/ (Year: 2023).

2 Pack Grease Needle Nozzle with Hardened Steel Tips, Tsinghwang, Amazon.com, [Post date: Dec. 12, 2022], [Site seen on Jul. 25, 2023], Seen at URL: https://www.amazon.com/Hardened-Dispenser-Fittings-Adapter-Threads/dp/B0BNXL7R4X (Year: 2022).

Hypervolt Bluetooth, amazon.com, first available date Jul. 31, 2020 [online], [site visited Aug. 2, 2023], Available from Internet, URL: https://www.amazon.com/Hypervolt-Bluetooth-Featuring-Quiet-Technology/dp/B08F2PN6CB (Year: 2023).

RENPHO Active Massage Gun, amazon.com, first available date Mar. 9, 2020 [online], [site visited Aug. 2, 2023], Available from the Internet, URL: https://www.amazon.com/Powerful-Portable-RENPHO-Percussion-Handheld/dp/B085NTR26K (Year: 2020).

Bob and Brad X6 Pro Massage Gun, amazon.com, first available date Aug. 22, 2021, [online], [site visited Aug. 2, 2023], Available from the Internet, URL: https://www.amazon.com/BOB-BRAD-X6-Pro-Professional/dp/B0983GZJHZ (Year: 2021).

Muchmore Racing Racing Blower, muchmoreracing.net, [online], [site visited Aug. 2, 2023], Available from the Internet, URL: http://www.muchmoreracing.net/product-view.php?pidx=3127 (Year: 2023).

* cited by examiner

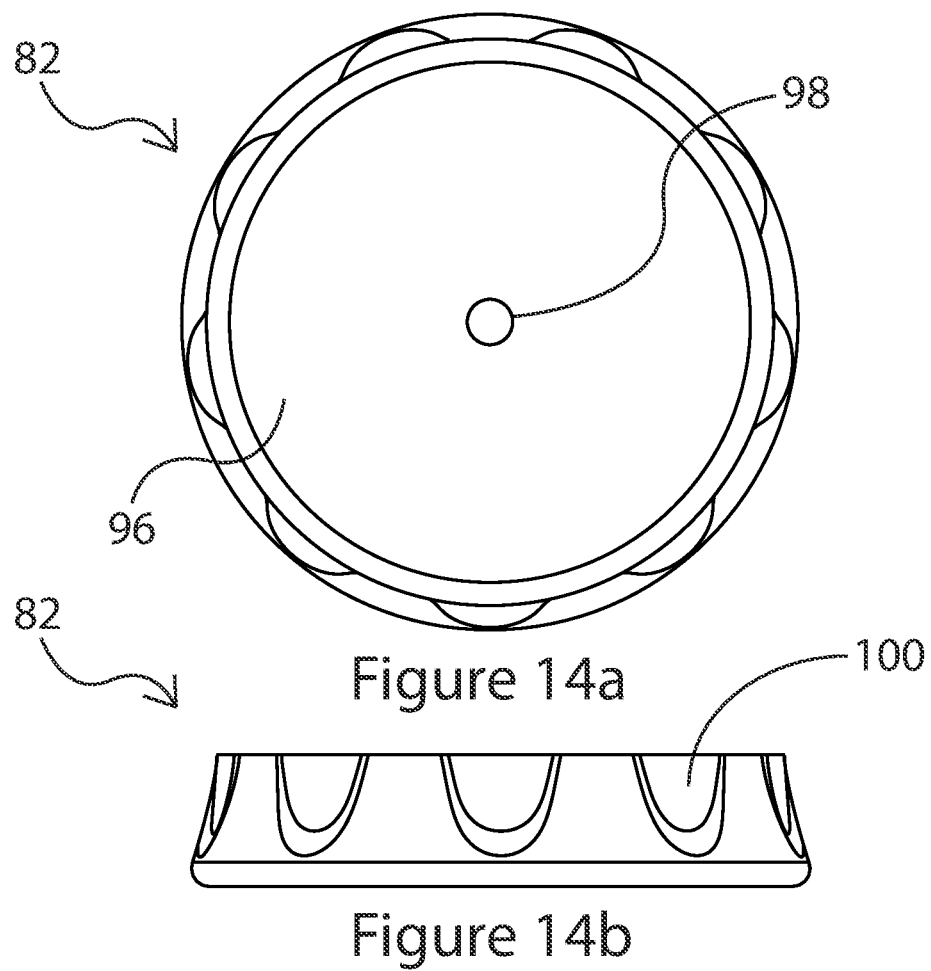
Figure 14a
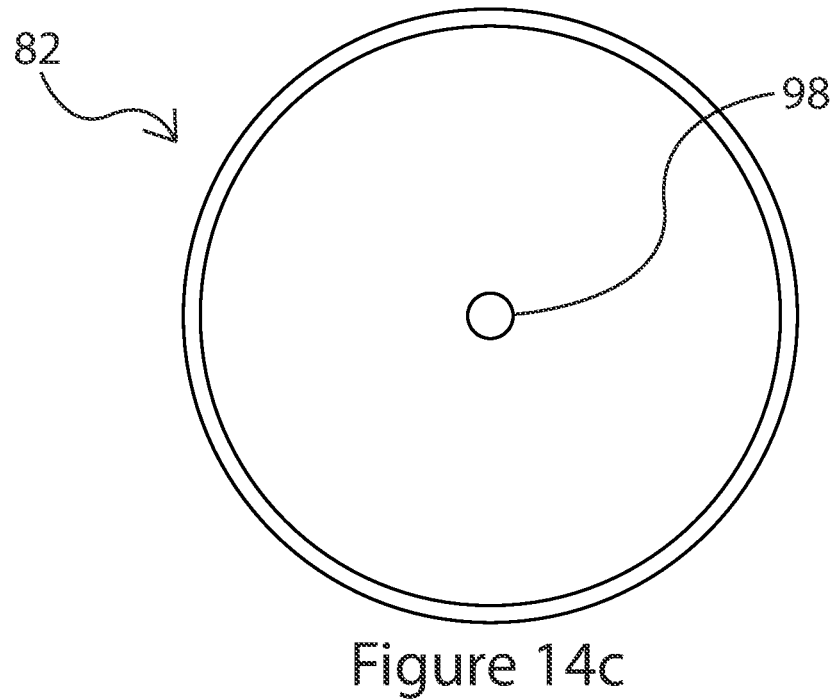
Figure 14b
Figure 14c ent. It is stated
MICRO-NEEDLING ARRAY TREATMENT ASSEMBLY

CROSS-REFERENCE TO RELATED APPLICATIONS

This application is a continuation in part of and claims the benefit of priority of U.S. Design patent application Ser. No. 29/884,654, filed Mar. 17, 2023, titled "Micro-Needle Tip Assembly"; U.S. Design patent application Ser. No. 29/884,664, filed Mar. 17, 2023, titled "Needle Tip Connector"; and U.S. Design patent application Ser. No. 29/884,655, filed Mar. 17, 2023, titled "Micro-Channeling Device"; which are all herein incorporated by reference.

FIELD

This patent application generally relates to a system for improving the appearance of skin. More specifically, it relates to a system for improving the appearance of skin that uses an electrically-driven micro-needling device along with a replaceable micro-needle array assembly.

BACKGROUND

Micro-needling was originally known as percutaneous collagen induction therapy (PCIT). Micro-needling is now a well-documented treatment for atrophic acne scars and improving the appearance of the skin. The therapeutic indications for this treatment option have increased over the last few years to include transdermal drug delivery, treatment of varicella and stretch mark scars, and improving the appearance of periorbital melanosis. Previously used on its own, it is now increasingly combined with other modalities to obtain ideal results. Micro-needling has been proven to increase absorption of topical medications into the skin by over 300 percent.

Micro-needling, as the term indicates, means the use of needles or "micro-needles" to achieve a therapeutic effect. Orentreich et al in 1995 successfully reported the use of needles in the treatment of acne scars. This was followed by the use of a tattoo pistol for needle dermabrasion by Camirand and then Doucet in 1997 for the treatment of scars. The technique of micro-needling was further innovated by Fernandes in 2006. Micro-needling as a treatment option in post-acne scars has been described by many clinical studies to date.

Micro-needling relies on the principle of neocollagenesis and neovascularisation that occurs as a result of the release of growth factors following needle piercing of the stratum corneum. These growth factors are believed to be responsible for the beneficial effects of the procedure in the treatment of scars and photo aging. Two hypotheses have been proposed to explain the mechanism of action of micro-needling: First: Formation of micro-channels with resultant healing response. Previously, it was proposed that following micro-needling, thousands of micro-channels or tiny wounds are produced through the epidermis into the papillary dermis of treated skin. These micro-channels create a confluent zone of superficial bleeding that acts as a powerful stimulus for the release of various growth factors such as platelet derived growth factor (PGF), transforming growth factor alpha and beta (TGF-α and TGF-β), and fibroblast growth factor (FGF), which initiate the normal process of wound healing by stimulating the migration and proliferation of fibroblasts that promote collagen deposition. Second: Production of a demarcation current. It has been hypothesized by Liebl that when the micro-needles penetrate the skin, a demarcation current is produced among cells rather than wounds. It is the demarcation current that triggers a cascade of growth factors that stimulate the healing phase. This hypothesis, based on the generation of bioelectricity, was proven by Jaffe. In resting state, the interior of epidermal cells have a negative electric potential of −70 mV whereas interstitium and epidermal surfaces have a positive potential. Epidermal injury causes the release of potassium and proteins into the interior of epidermal cells, further decreasing the electric potential to −120 mV or less. This leads to an increase in the potential difference between the interior of the cell and the exterior environment. It is stated that this potential difference triggers the migration of fibroblasts to the site of injury where they proliferate and lay down collagen.

Clinical experience now demonstrates that infliction of direct trauma such as that seen with ablative laser treatments is not necessary to promote dermal thickening. Rather, minimal trauma resulting from the use of short needles (under 2 mm) during medical micro-needling is sufficient to cause release of growth factors and cytokines from keratinocytes within the epidermis. These bio-signals, in turn, result in the sequential cascading release of bio-signals into deeper layers, ultimately resulting in cellular proliferation and dermal thickening, as shown by Setterfield.

Medical micro-needling is currently being researched with the use of human stem cells for a new, natural approach to improve the appearance of both skin and hair. With this system, specially formulated human bone marrow-derived mesenchymal stem cell growth factor serums are used which safely penetrate the perforations made from micro-needling to enhance production of new collagen and elastin in the skin or to repair damaged hair follicles in the scalp.

Micro-needle rollers were the original instruments used for medical micro-needling. A micro-needle roller is a simple, hand-held instrument consisting of a handle with a cylinder studded with sterile, fine, stainless steel needles of 0.5-2 mm in length. There are approximately one hundred ninety-two needles and they are spaced at regular distances from each other. In order to achieve a uniform depth of penetration, the needles are placed at an inclination of 15-degrees in relation to the surface of the micro-needle roller. The micro-needles are synthesized by reactive-ion etching techniques on silicon or medical-grade stainless steel. To achieve the therapeutic benefit, this needle studded cylinder is rolled on the skin in multiple directions and hence the name micro-needle roller. As the therapeutic use of micro-needling has been extended beyond scar management, various modifications have occurred since the micro-needle roller was originally introduced. Home-care micro-needle rollers, with needles less than 0.1 mm in length, have been introduced for transdermal delivery of other anti-aging products.

Unlike hand held manual devices, motorized micro-needling pens are powered stamping devices using batteries or electrical sources. Advantages of these motorized micro-needling pens include treating small areas (as opposed to the entire face), and greater control in hard-to-treat areas such as the nose, upper lip and around the eyes.

Current motorized devices, however, are deficient in that they use a disposable cartridge tip having a relatively small array of needles as the treatment tip and they reciprocates within a plastic tube. Because of the small size of the treatment area of these tips, relatively small areas of skin are exposed to the treatment, resulting in the possibility of a dragging motion to cover the entire treated area within a reasonable amount of time. This dragging motion can create a "scratching" pattern in the skin and a subsequent increased amount of tissue trauma. Increased tissue trauma causes excessive swelling and inflammation and results in less optimal conditions for transcutaneous penetration of topically applied serums after the treatment. These tips have adjustable-length needles but have no way of ensuring the depth of penetration is not "operator-dependent". The amount of force placed upon the device by the operator at the time of treatment will affect the depth of needle penetration. Also, the reciprocal motion of the needle tip can create suction within the tube and may cause "backflow contamination" due to tissue fluids travelling into the cartridge and then into the motorized device itself. The transfer of rotational to linear motion in these devices lacks a robust mechanism and can therefore result in device failures. The present invention aims to improve upon these deficiencies.

SUMMARY

In one implementation, the present disclosure is directed to a micro-needling system. The micro-needling system comprises a pushrod capable of linear reciprocating motion along a reciprocation axis; a rotary motor capable of rotating a motor shaft around a rotation axis, the rotation axis is perpendicular to the reciprocation axis; a crank working in cooperation with a crank arm to convert rotation motion of the rotating motor shaft into linear reciprocating motion of the pushrod; and a needle tip connector for connecting a micro-needle array assembly to the pushrod.

In another implementation, the present disclosure is directed to a micro-needle array assembly. The assembly comprises a disc-shaped attachment plate having a connection side and a needle side, an array of needles emanating from the needle side, and a disc-shaped safety cap for covering the needles.

BRIEF DESCRIPTION OF DRAWINGS

For the purposes of illustrating the invention, the drawings show aspects of one or more embodiments of the invention. However, it should be understood that the present invention is not limited to the precise arrangements and instrumentalities shown in the drawings, wherein:

FIG. 8b is a sectional view along 8b-8b of FIG. 8a;

FIG. 14a is a top view of the safety cap associated with the micro-needling assembly shown in FIG. 10;

FIG. 14b is a side view of the safety cap associated with the micro-needling assembly shown in FIG. 10;

FIG. 14c is a bottom view of the safety cap associated with the micro-needling assembly shown in FIG. 10;

DETAILED DESCRIPTION

Figure 1:
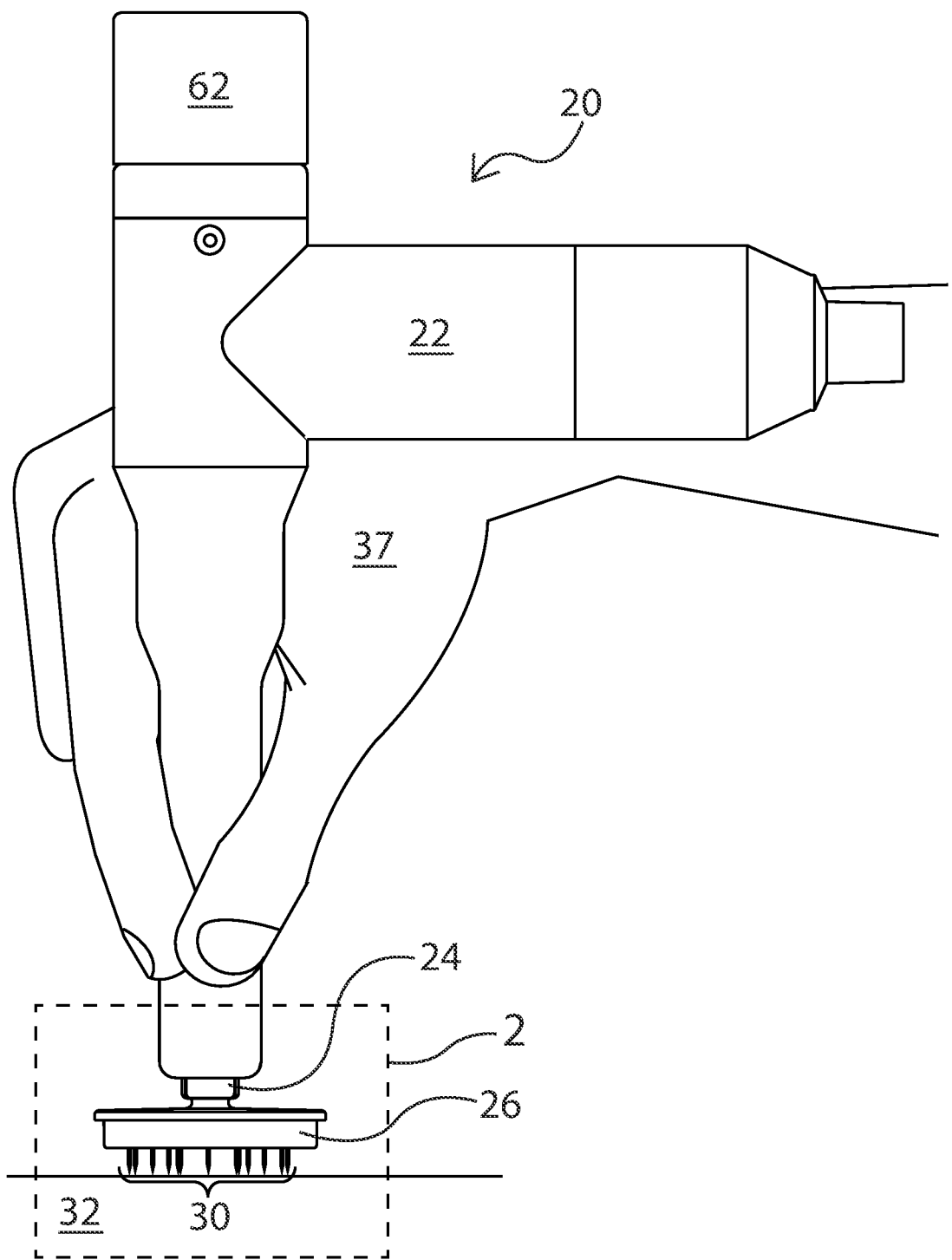
FIG. 1 is a side view of one embodiment of the micro-needling system in accordance with the present invention.
Figure 3:
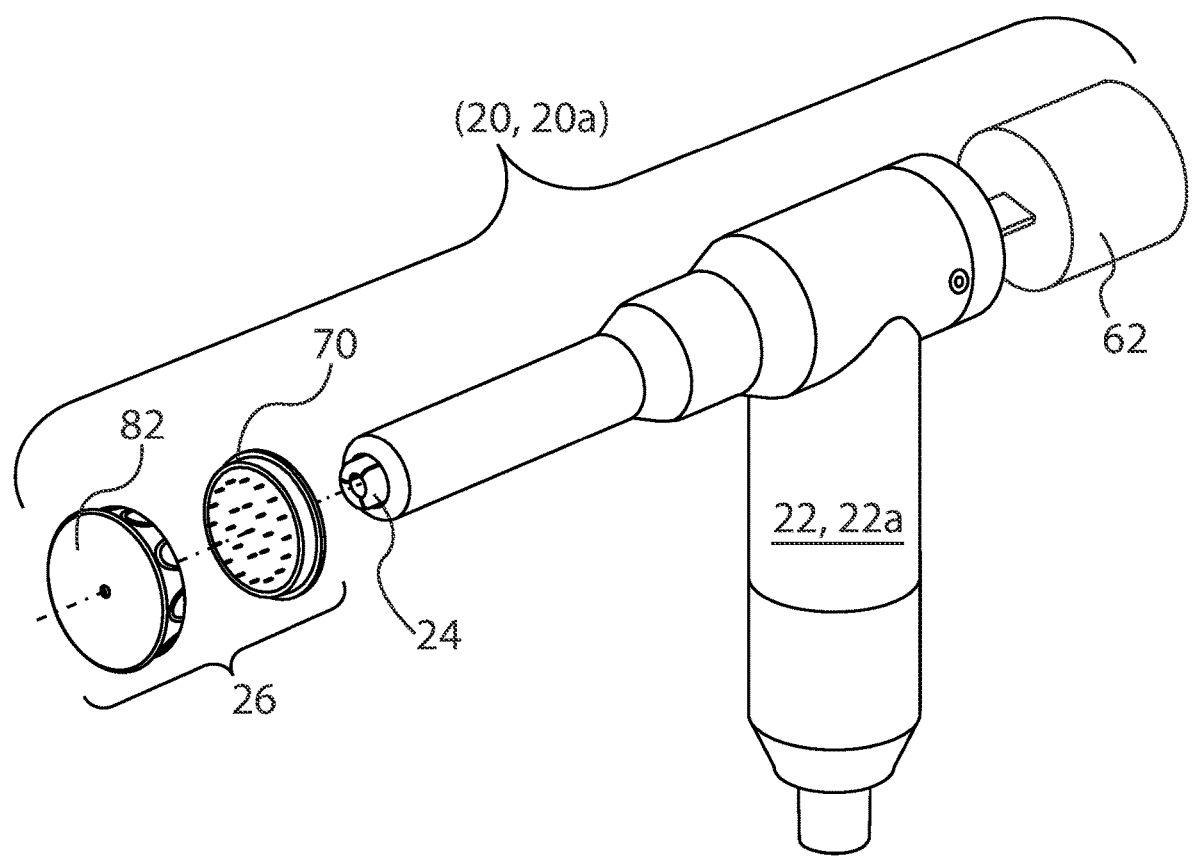
FIG. 3 is an exploded view of FIG. 1 illustrating the major components of the micro-needling system.
Figure 4:
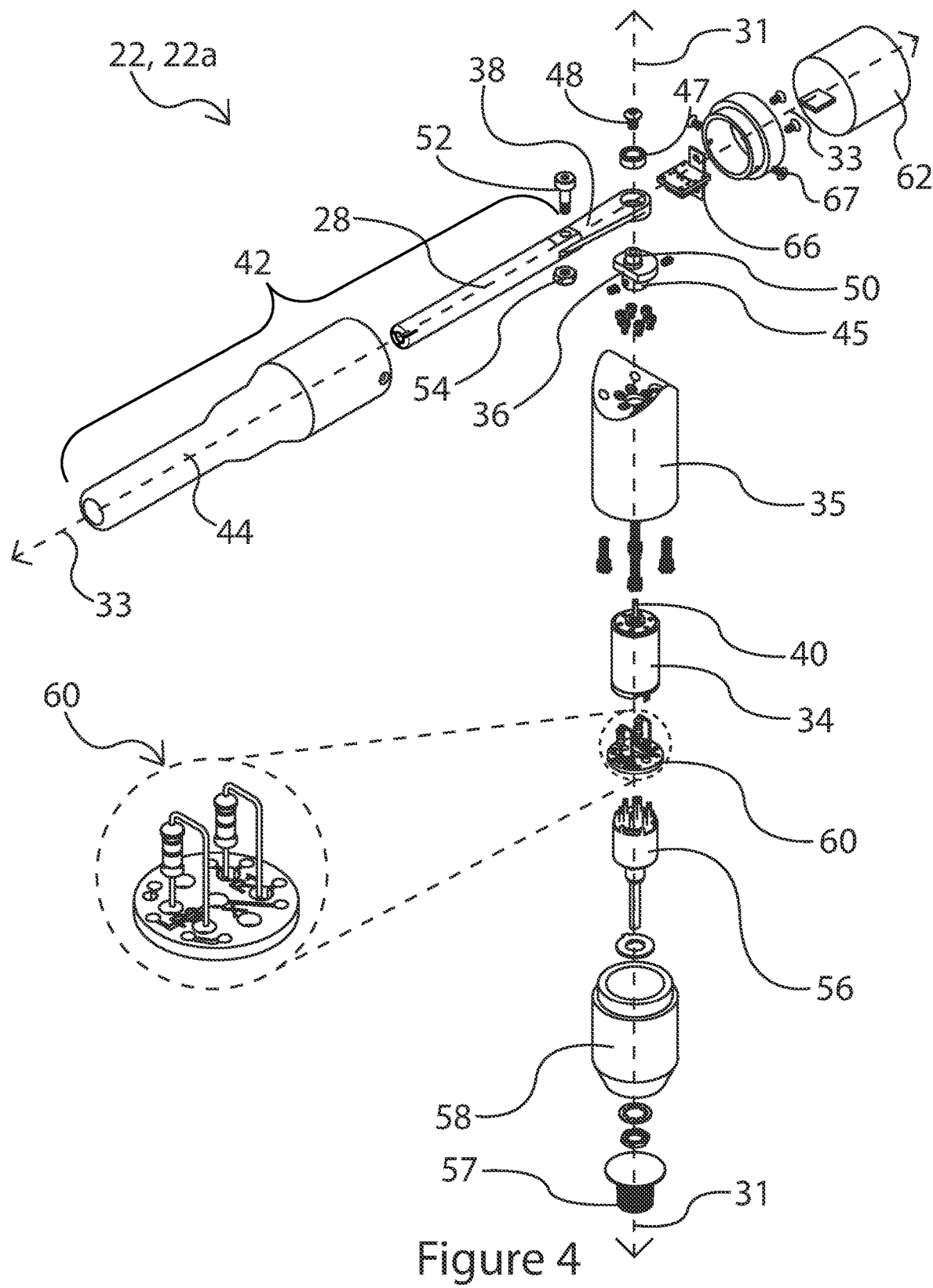
FIG. 4 is an exploded view of the micro-channeling device shown in FIG. 3 illustrating detailed elements of the device.
Figure 5:
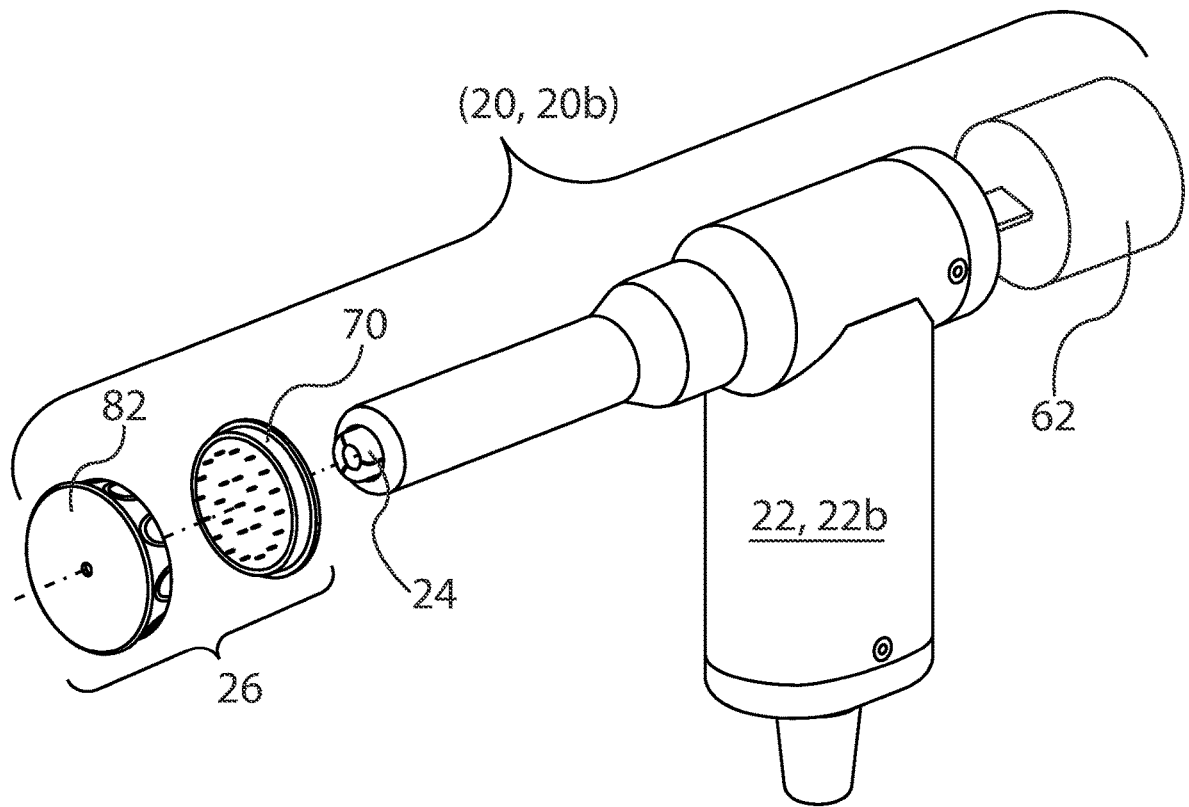
FIG. 5 is an exploded view of another embodiment of the micro-needling system shown in FIG. 1, illustrating the major components associated with this embodiment.
Figure 6:
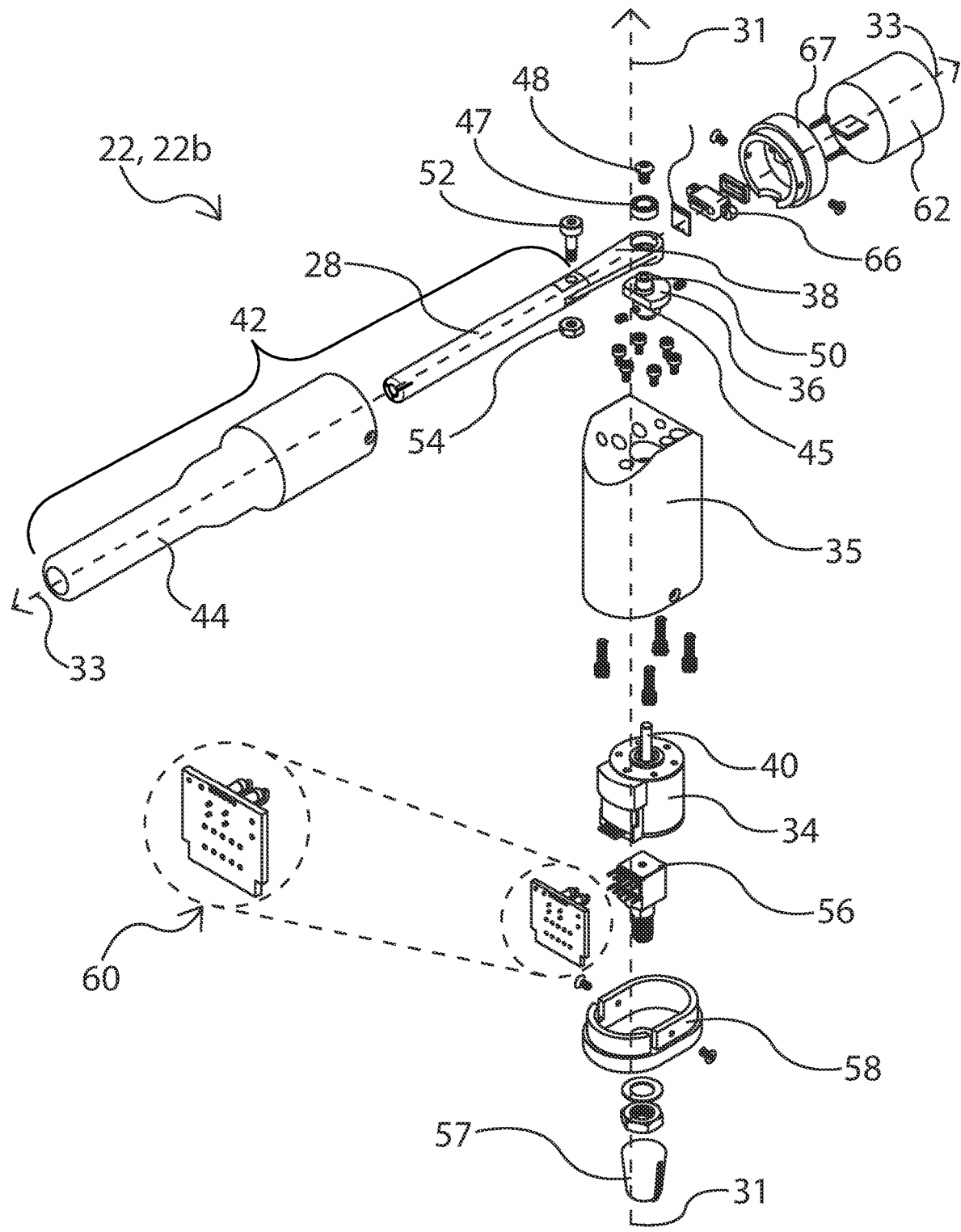
FIG. 6 is an exploded view of the micro-channeling device shown in FIG. 5 illustrating detailed elements of the device.
Figure 7A:
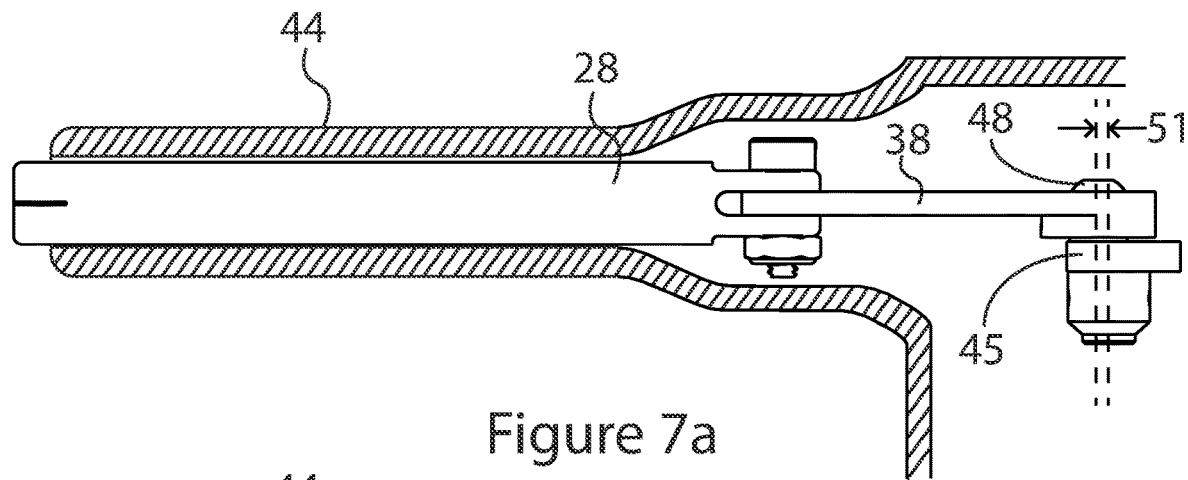
FIG. 7a is side, partial-sectional view of the crank, crank arm and guidance system of the micro-needling system of FIG. 1 that turns rotational motion of the motor into linear motion of the push rod.
Figure 7B:
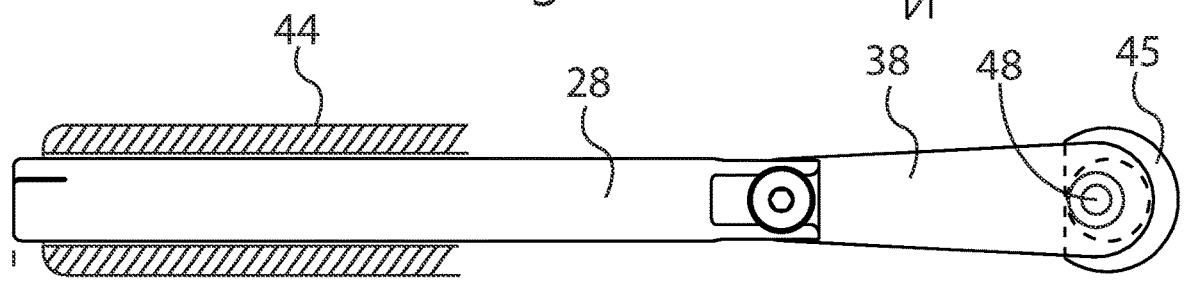
FIG. 7b is top, partial-sectional view of a first step in the operation of micro-needling system illustrated in FIG. 7a showing a first linear position of the pushrod that is related to the rotational location of the crank.
Figure 7C:
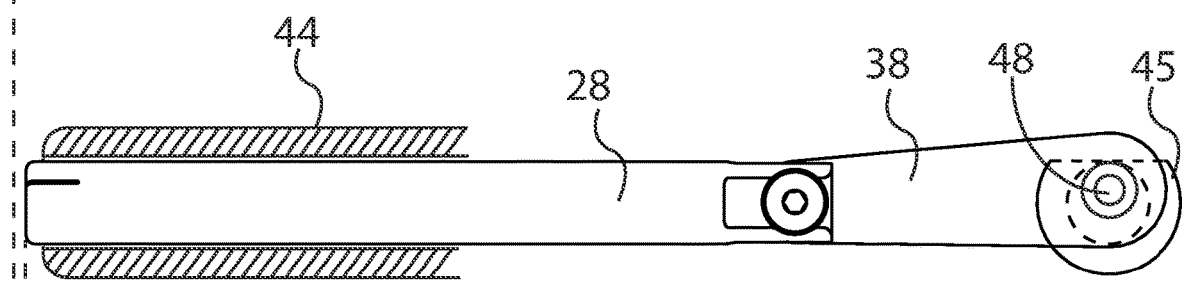
FIG. 7c is top, partial-sectional view of a second step in the operation of micro-needling system illustrated in FIG. 7b showing a second linear position of the pushrod that is related to the rotational location of the crank.
Figure 7D:
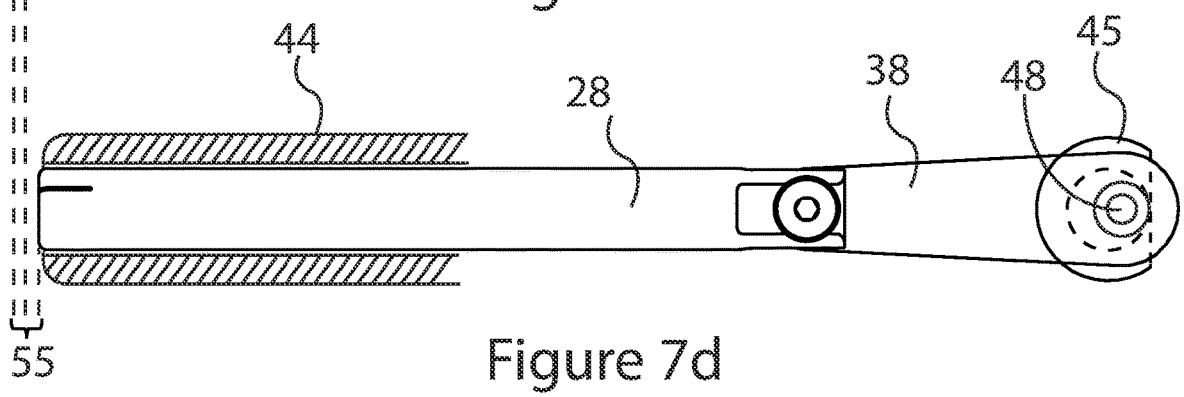
FIG. 7d is a top, partial-sectional view of a third step in the operation of the micro-needling system illustrated in FIG. 7c showing a third linear position of the pushrod that is related to the rotational location of the crank.
Figure 8A:
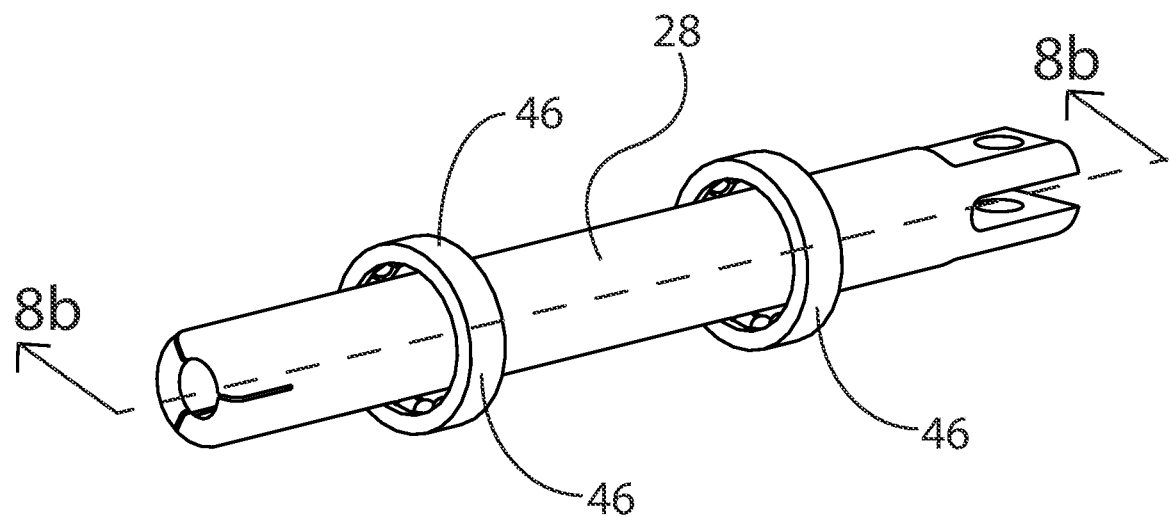
FIG. 8a is a perspective view of one embodiment for holding the push rod within the barrel of the micro-channeling device of FIG. 1.
Figure 8B:
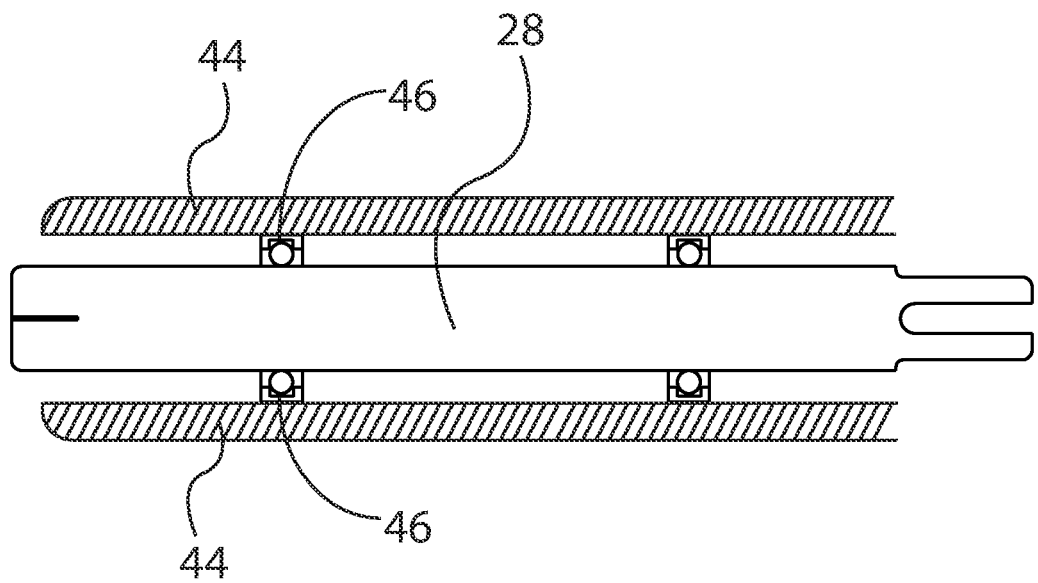

Micro-needling system 20 (20a and 20b) is illustrated in FIGS. 1-18. Micro-needling system 20 comprises any combination or sub-combination of micro-channeling device 22, needle tip connector 24 and micro-needling assembly 26, FIG. 1. Micro-needling system 20 may include different embodiments of these components that work together to form a single micro-needling system. For example, FIGS. 3 and 4 illustrate a first embodiment of micro-channeling device (22, 22a) as a basic device and FIGS. 5 and 6 illustrate a second embodiment of micro-channeling device (22, 22b) that has an AC powered motor with better durability and vibration control. Similarly, variations of needle tip connector 24 are shown in FIGS. 17a and 17b illustrating different options for finger 103 flex related to the materials of fabrication. And similarly, variations of micro-needling assembly 26 are shown in FIGS. 13a-c; differences may include size of disc, needle array patterns, density of needles, length of needles, etc.

Figure 2:
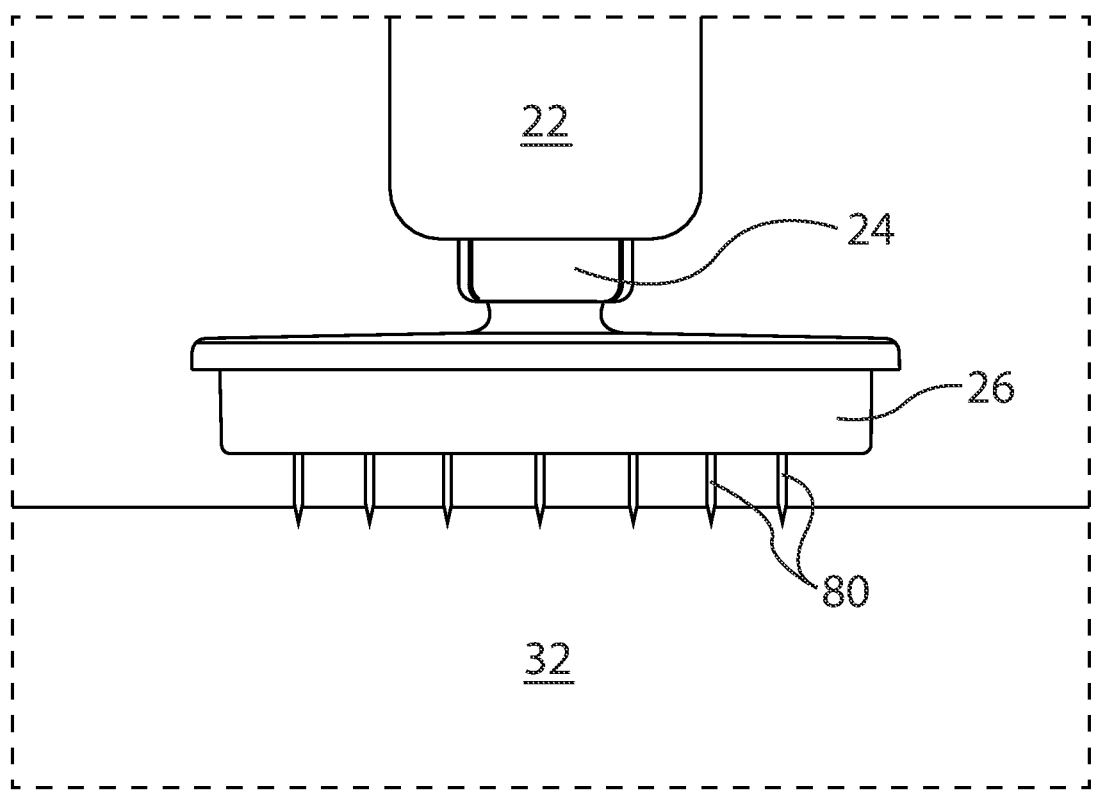
FIG. 2 is an enlarged side view of the area labeled 2 in FIG. 1 illustrating details of the micro-needle array system and use to improve the appearance of skin.

Micro-channeling device 22 is an electrically driven device that transforms rotation motion of motor 34 around rotation axis 31 into linear motion along reciprocation axis 33 that drives needle array 30 in and out of skin 32 when placed upon the skin, FIG. 2. Handle 35 has been designed to be at right angles to the channeling direction so as to facilitate an ergonomic approach to hold micro-channeling device 22 by resting the device on the user's hand 37. Needle tip connector 24 provides a rapid and secure way for changing between different micro-needling assemblies 26.

As illustrated in FIGS. 4, 6, 7a-d and 8a-b, micro-channeling device 22 (22a, 22b) comprises pushrod 28 capable of linear reciprocating motion along a reciprocation axis 33. Micro-channeling device 26 further comprises a rotary motor 28 capable of rotating a motor shaft 40 around a rotation axis 31. Rotation axis 31 is perpendicular to reciprocation axis 33. Micro-channeling device 26 further comprises crank 36 working in cooperation with crank arm 38 to turn rotational motion of the rotating motor shaft 40 into linear reciprocating motion of pushrod 28. Barrel 44, handle 35, barrel cap 67 and switch cap 58 make up the micro-channeling device housing that holds all components.

A mechanical guidance system 42 is defined by the mechanical restriction of at least a portion of pushrod's outer surface, physically restricting the pushrod's non-linear lateral motion distance to the inner surface of barrel 44, when driven by crank arm 38. Mechanical guidance system 42 provides physical engagement with pushrod 28 so that the pushrod's motion is restricted to linear reciprocating motion along reciprocation axis 33, FIGS. 7a-7d. Alternatively, mechanical guidance systems 42 may use a plurality of bushings, bearings, roller bearings 46, ball bearings, etc.; preferably only two bearings with one on each end, FIGS. 8a and 8b. Preferably at least one of the roller bearings 46 is sealed against ingress of contaminants Crank 36 is driven by rotating motor shaft 40, FIGS. 7a-d. Motor 28 has a motor speed control system. Crank 36 includes one side with a centrally located motor connector 45 that connects to motor shaft 40. Crank 36 includes on the opposite side crank arm connector 50 that's center is offset by offset distance 51 from the crank's center and connected via bearing 47 and bearing screw 48. Crank arm 38 is connected to pushrod 28 via pushrod screw 52 and locknut 54. When crank 36 is rotated by motor 34, crank arm connector 50 is rotated in a circular motion around rotation axis 31. This circular motion drives the end of crank arm 38, which is connected to by crank arm connector 50, to have combined circular motion and reciprocating motion. The other end of crank arm 38 is connected to pushrod 28 that resides within barrel 44 and is forced by guidance system 42 to turn the circular motion and reciprocating motion into only reciprocating motion for the pushrod. Crank arm 38 effectively converts the rotational motion of the rotating motor shaft 40 into linear reciprocating motion of pushrod 28. This range of reciprocating motion is generally between the length of the longest protruding part of the protrusion side of the array assembly and shorter than the distance that would significantly increase device inertia that would cause increased device vibration while further causing decreased efficiency. The length of the needles act as one limit to how much penetration into the skin occurs. As a result, the medical procedure's reciprocal motion is generally in the range of the needles which are 0.25 mm to 1.5 mm long (needle tip travel distance) even though device 20 may have the capability to travel more. The crank has a throw-length 55 of 0.040", which generates a stroke-length of 0.080" or 1-2 mm. Typical skin penetration ends up in the range zero to 1.5 mm. Crank 36 is preferably a balanced crank that limits the amount of vibration and provides a smoother reciprocal motion.

Micro-channeling device 22 further includes a switch 56 connected to handle 35. Control of switch 56 is accomplished via a rotational, multi-position switch control knob 57 that is actuated through engagement the switch control knob. Switch control knob 57 has operation options such as off, low-speed, high-speed, etc. As used in this disclosure, speed refers to reciprocating motion of strokes per minute as set by rpm of motor 34. Speeds are generally in the range of 4700 rpm to 6375 rpm. PCB 60 serves to provide motor speed control. As shown in FIGS. 4 and 6, this is accomplished by way of varying frequencies sent to motor 34, a VVVF (variable voltage variable frequency) type motor. Switch cap 58 rigidly attaches switch 56 with switch control knob 57 to the micro-channeling device housing.

Micro-channeling device 22 further includes a power source 62. Power is directed through power port 66 that resides within barrel cap 67. Power port may be a USB port. Micro-channeling device 22 may be powered by a battery or a direct connection to a power outlet.

Figure 9:
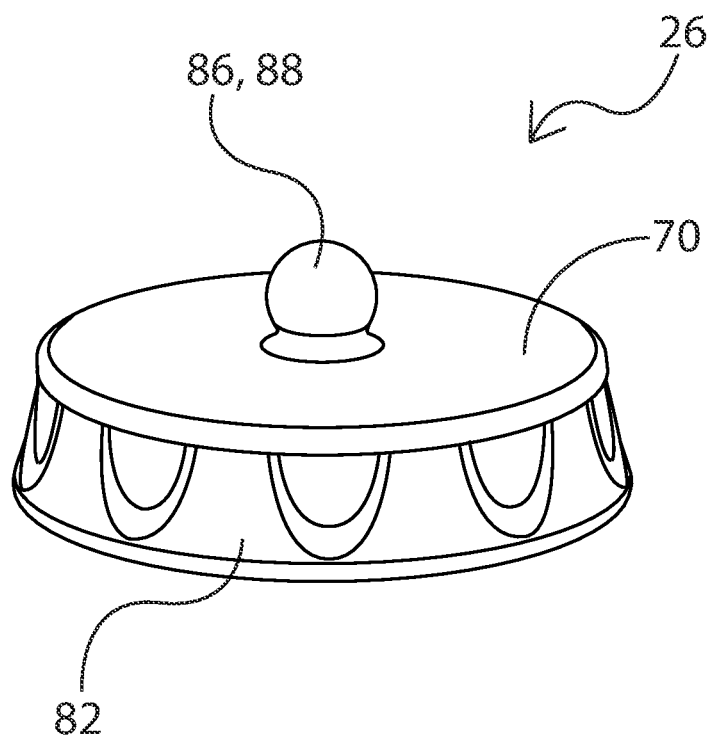
FIG. 9 is a perspective view of the micro-needling assembly shown in FIGS. 1, 2, 3 and 5.
Figure 10:
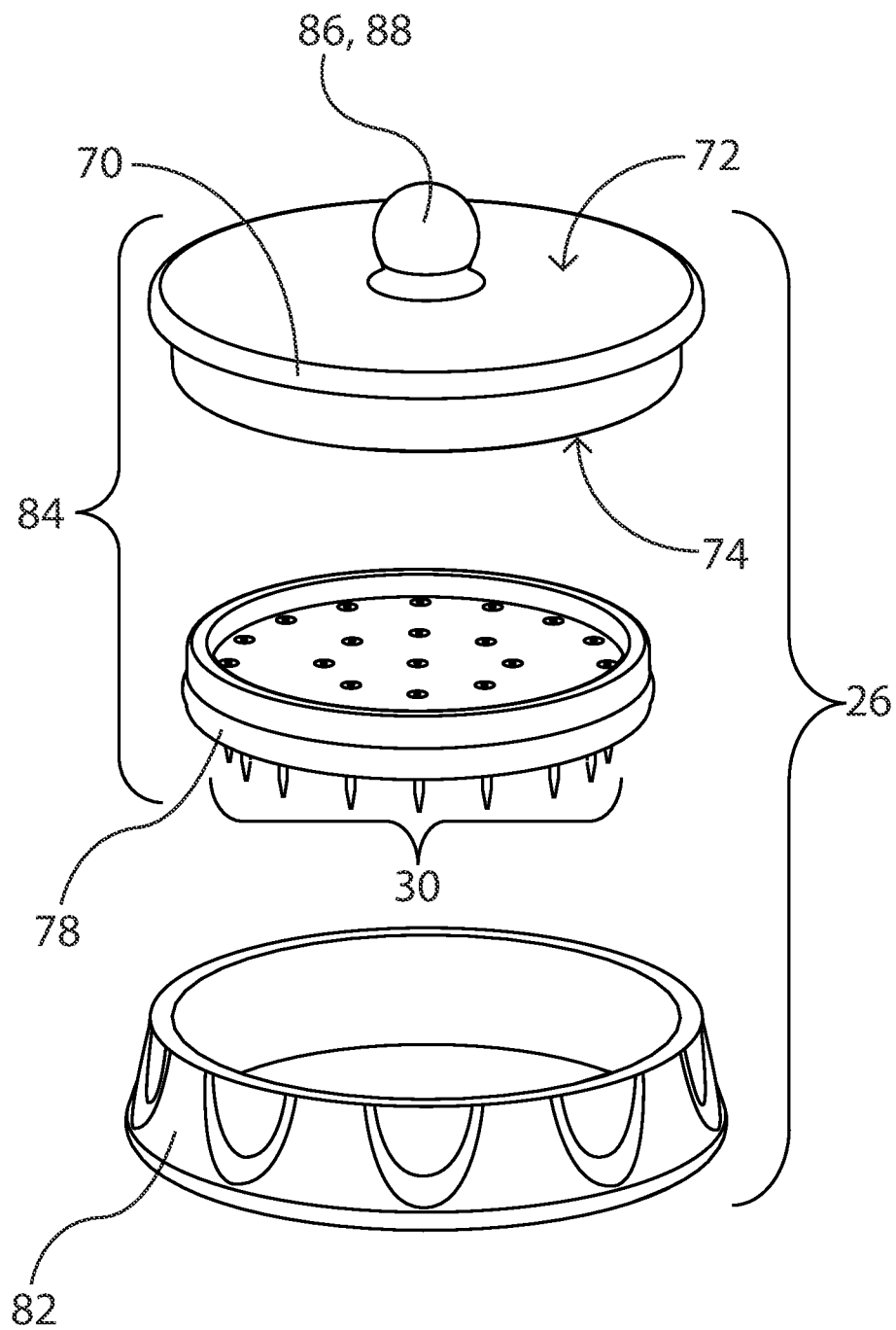
FIG. 10 is an exploded view of the micro-needling assembly shown in FIG. 9, illustrating the components associated with this embodiment.
Figure 11A:
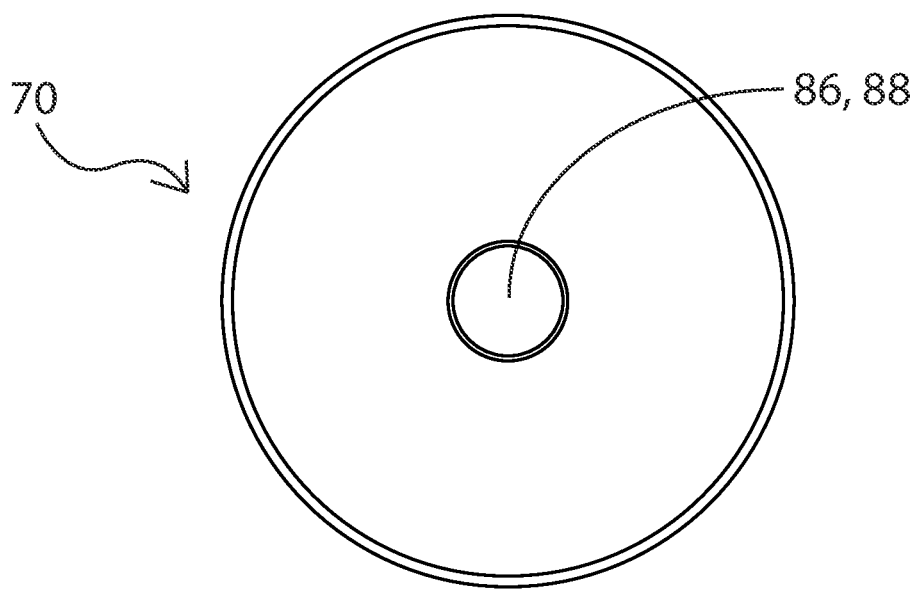
FIG. 11a is a top view of the attachment plate associated with the micro-needling assembly shown in FIG. 10.
Figure 11B:
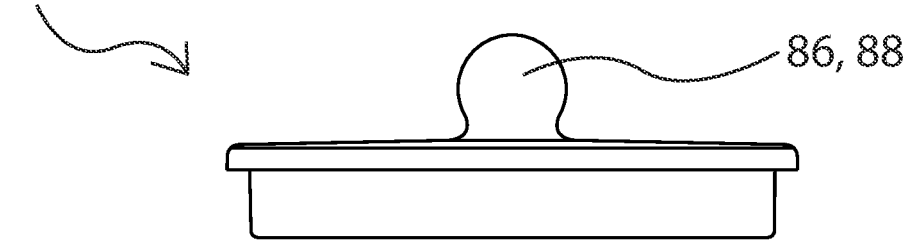
FIG. 11b is a side view of the attachment plate associated with the micro-needling assembly shown in FIG. 10.
Figure 11C:
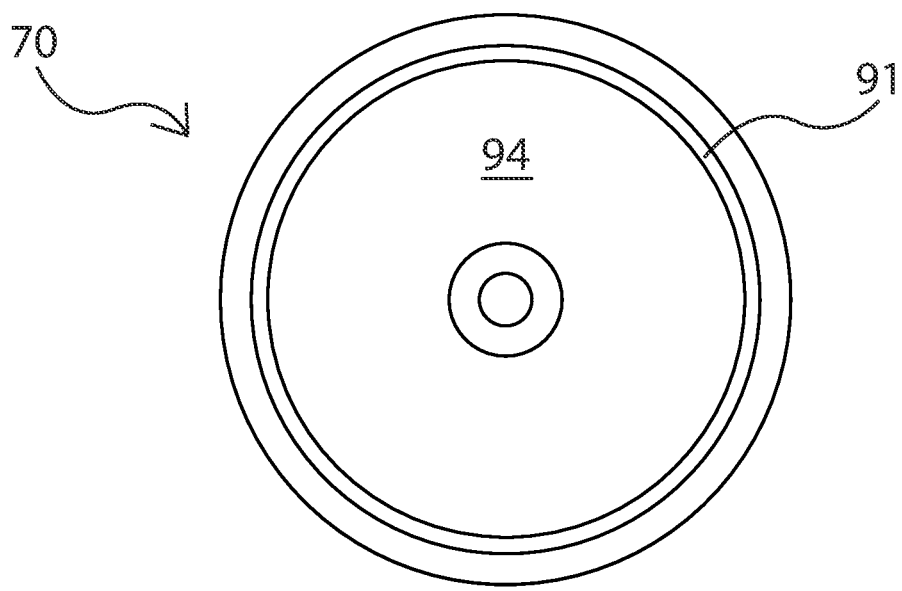
FIG. 11c is a bottom view of the attachment plate associated with the micro-needling assembly shown in FIG. 10.

Micro-needling assembly 26, FIGS. 9 and 10, comprises attachment plate 70 having a device connection side 72 and a needle side 74, needle mounting plate 78 with an array of needles 80 extending from the needle side, and a safety cap 82 for covering the needles. Attachment plate 70 and needle mounting plate 78 fit together by a press fit seal to create needle tip plate 84. It is critical that micro-needle assembly be disc-shaped and thin enough to fit into facial grooves and creases. The roundness of the disc provides a curved surface to get around facial parts such as the nose. The critical thickness is that needle tip plate with needles be less than 0.5-centimeters thick so that the needles can be used in tight areas such as folds and creases on the face such as the nasolabial sulcus, alar sulcus, philtrum, labial commissure, and labiomental groove. Lighter weight also allows the user to tap more delicately. The large area of the disc allows for a significant area of the skin to be treated without needing to slide the needles across the skin that can result in scratch lines.

Attachment plate 70 has a device connection side 72 and a needle side 74, FIGS. 10 and 11a-c. Device connection side 72 is fitted with a device connector 86. Device connector 86 mates with needle tip connector 24 of micro-channeling device 22, which fits within connection receptacle 102. Needle side 74 of attachment plate 70 has mounting plate recess 94 with an interior lip 91 for accepting needle mounting plate 78.

Figure 12A:
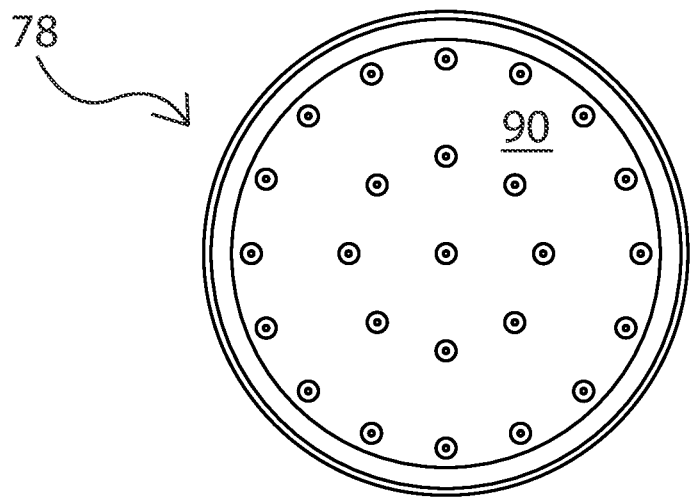
FIG. 12a is a top view of the needle mounting plate associated with the micro-needling assembly shown in FIG. 10.
Figure 12B:
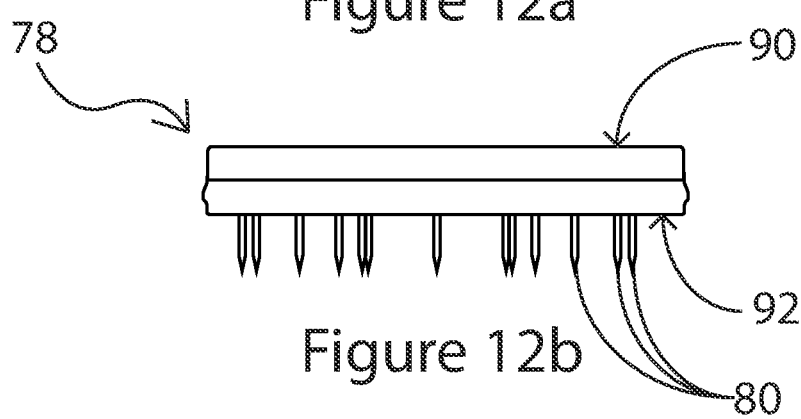
FIG. 12b is a side view of the needle mounting plate associated with the micro-needling assembly shown in FIG. 10.
Figure 12C:
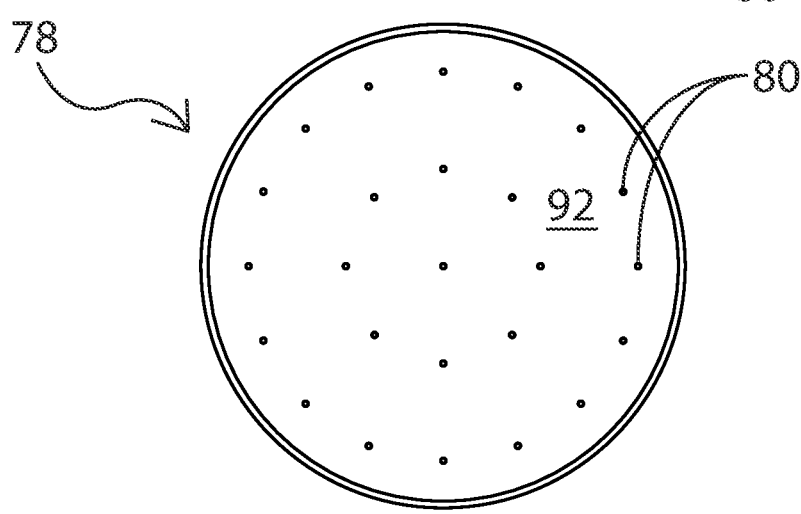
FIG. 12c is a bottom view of the needle mounting plate associated with the micro-needling assembly shown in FIG. 10.
Figure 13A:
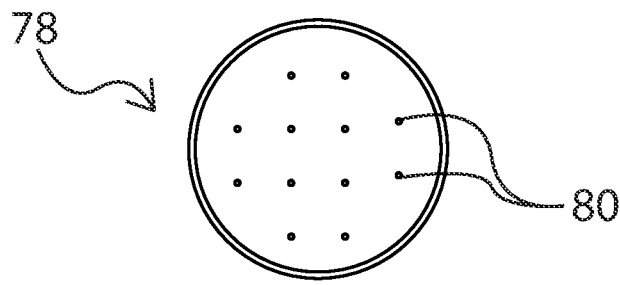
FIG. 13a is a bottom view of the needle mounting plat of FIGS. 12a-c, showing a first embodiment of needle placement.
Figure 13B:
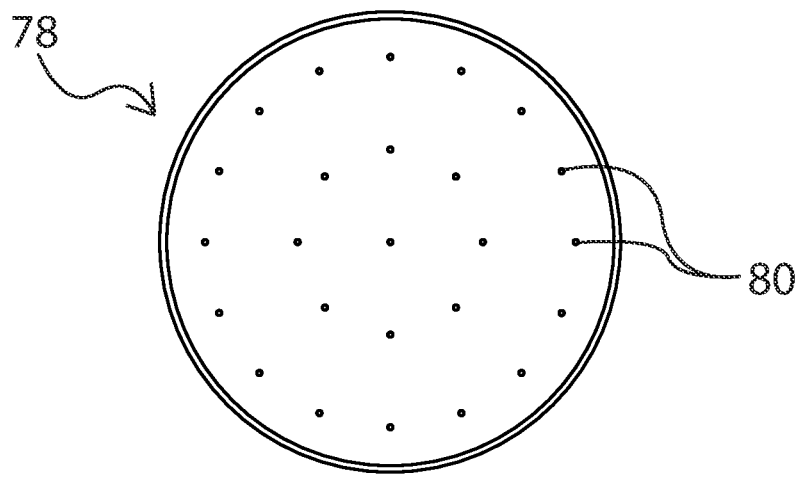
FIG. 13b is a bottom view of the needle mounting plat of FIGS. 12a-c, showing a second embodiment of needle placement.
Figure 13C:
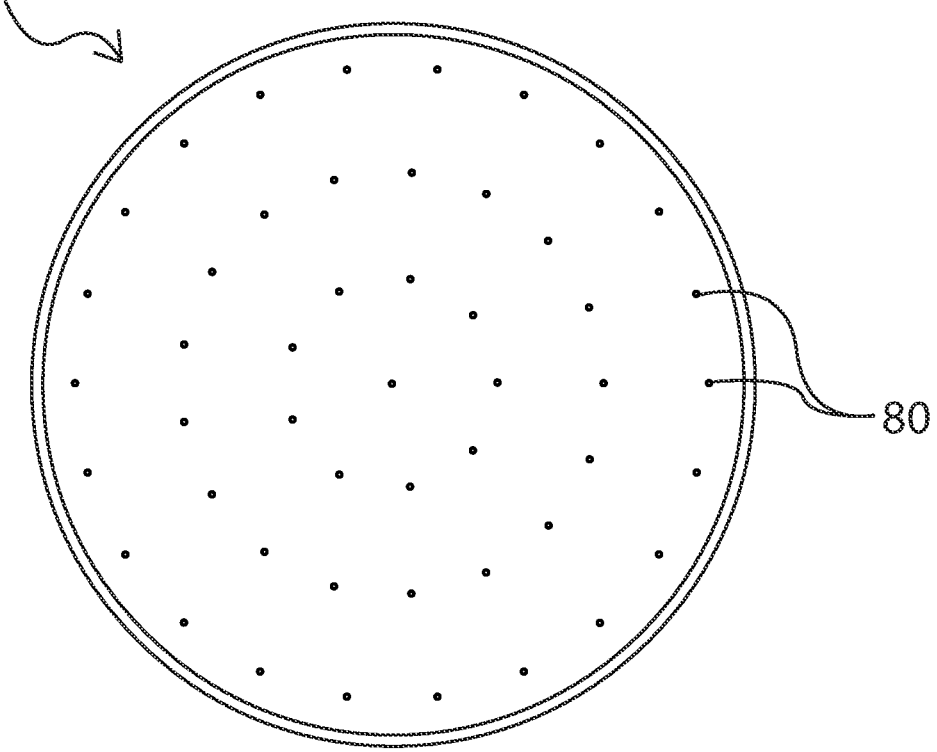
FIG. 13c is a bottom view of the needle mounting plat of FIGS. 12a-c, showing a third embodiment of needle placement.
Figure 15:
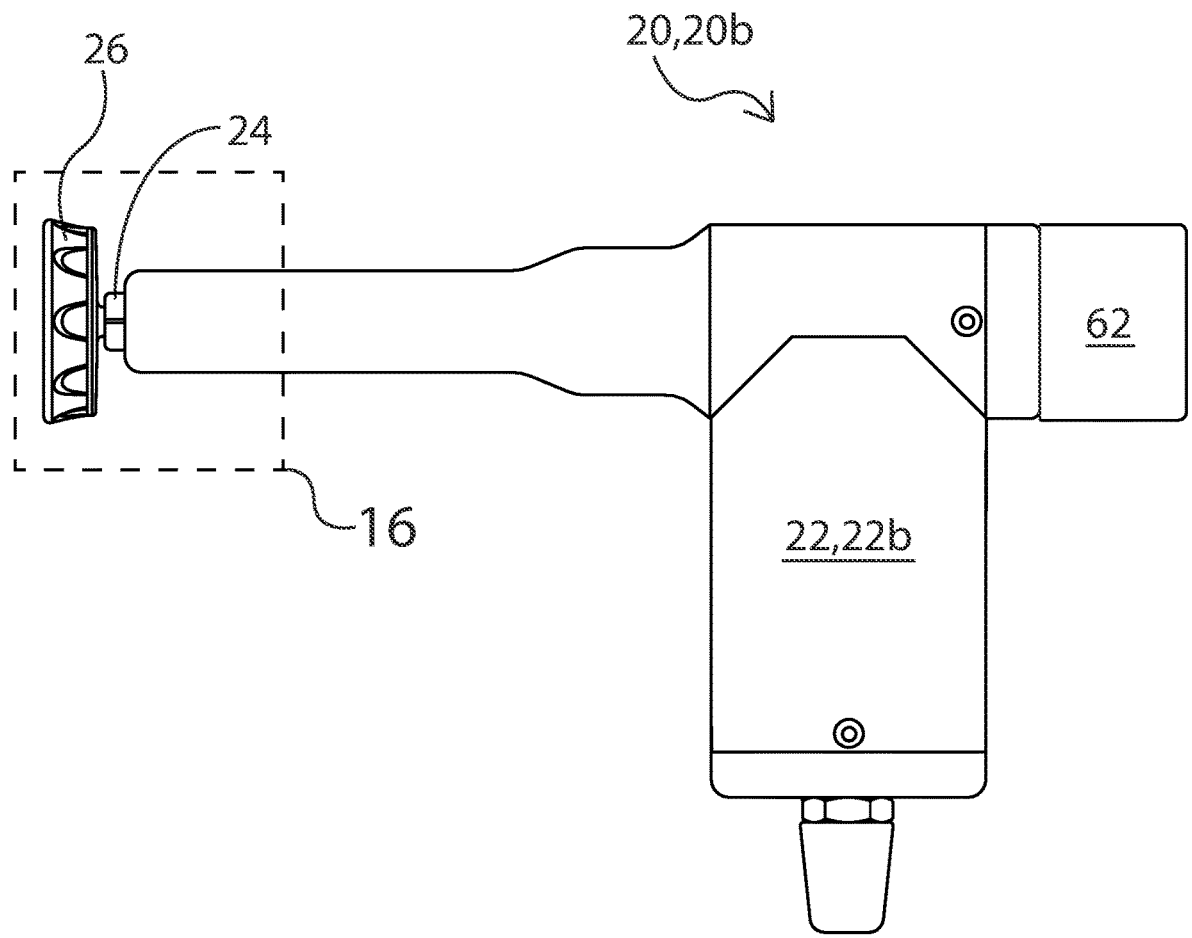
FIG. 15 is a side view of the micro-needling system in FIG. 1 with associated safety cap.

Needle mounting plate 78 has an attachment plate side 90 and a needle side 92, FIGS. 12a-c. The outer perimeter of needle mounting plate 78 is sized to fit within needle mounting plate recess 94 of attachment plate 70. Needles 80 can be molded, embedded, or press fit into needle mounting plate. The density and array pattern for needles is chosen depending on application. Different sized needle mounting plates and array patterns are shown in FIG. 13a-13c.

Needles 80 are preferably made of stainless steel or plastic. Needles 80 are generally 0.25 mm in diameter and lengths ranging from 0.25 mm to 1.5 mm. Needles 80 generally have a diameter of about 0.25 mm. Smaller diameter needles create less scaring. Too short of a needle and one cannot get serum in. Too long of a needle creates too much trauma. Also, the bigger the needle the more pain generated. Aestheticians are allowed to use shorter length needles and doctors can use longer length needles.

In another embodiment, needles 80 may be coated with medically approved coatings. These needles 80 can be coated individually. Coating options may include TiN (titanium nitride), and DLC (diamond like carbon). While there is no simple relationship between the coefficient of friction and the lubricity, there is literature of these properties having an inversely proportional relationship. In actual practice friction is often decreased by introducing lubricants or a lubricating film. Coatings having less friction provide less treatment discomfort. Both of the above mention coatings have previously been used for medical application and additionally both have an extremely low coefficient of friction. These coatings also have extremely high hardness.

Safety cap 82, FIGS. 14a-c, is designed to have a cap recess 96 that fits over needle mounting plate 78 to protect needles 80 when they are not actively being used on a patient. Safety cap 82 has a snap fit to secure the cap with needle mounting plate 78. Air hole 98 is provided to allow excess air to escape from the safety cap so as to facilitate easy on and off. The outer perimeter of safety cap 82 is provided with a grip enhancing pattern or material to facilitate easy application and removal of the safety cap. Gripping patterns may include scallops 100, knurling, dots, or other textures. Safety cap 82 may also have a coating or layer applied to facilitate good gripping properties. Examples include synthetic leathers, natural leathers, polyurethane (PU), latex, nitrile, silicone, PVC, pressure compressible material, etc.

Details of needle tip connector 24 are shown in FIGS. 15-18. Needle tip connector includes a connection receptacle 102 with connector slots 104 on pushrod 28 for receiving device connector 86. It is critical that device connector 86 be a ball connector 88, which is perpendicular to the connection side 72 of mounting plate 70. While other mechanical shapes are possible, it is necessary to have both a snap fit and the ability of micro-needle assembly to rotate to the contour of the skin surface being treated. A ball connector accomplishes this. Snap fitting components typically contain at least one insertion dimension that is larger than the capturing opening to provide for the tight fit. As such, ball connector 88 has a larger diameter than the inside diameter of flange 89.

Figure 16:
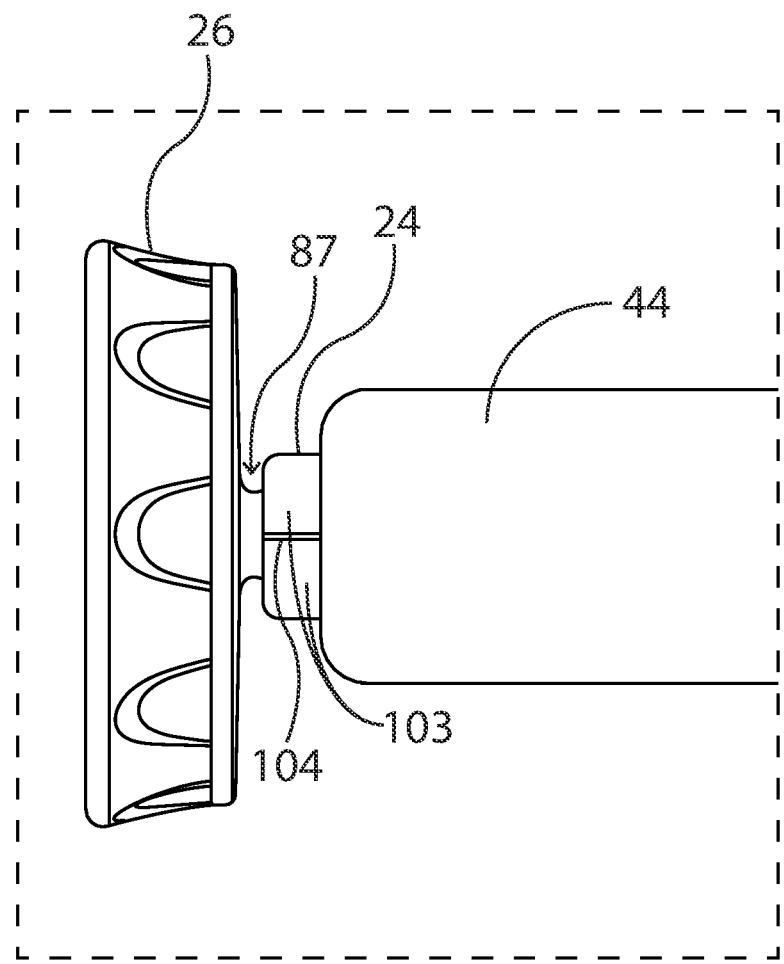
FIG. 16 is an enlarged view of the area labeled 16 in FIG. 15 illustrating details of the micro-needling system.
Figure 17A:
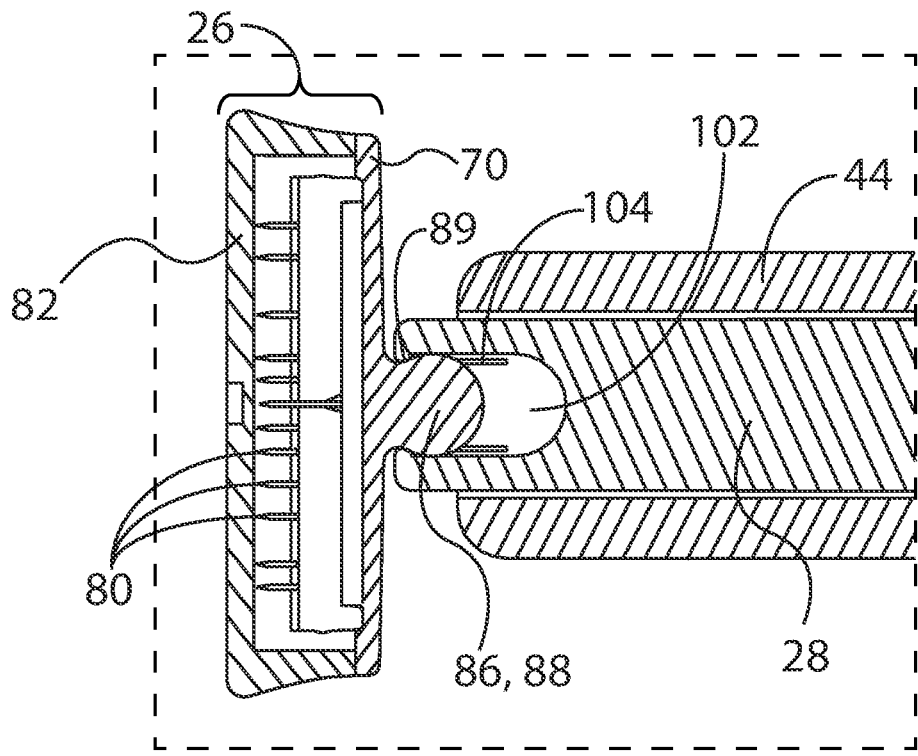
FIG. 17a is a sectional view of FIG. 16 showing a first embodiment for the connection recess.
Figure 17B:
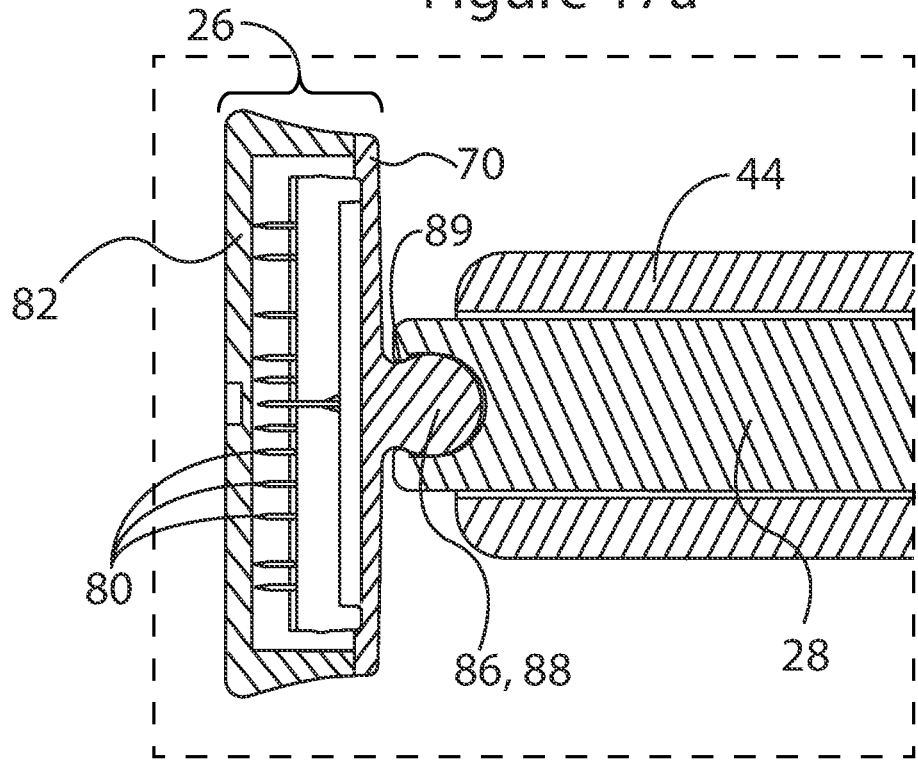
FIG. 17b is a sectional view of FIG. 16 showing a second embodiment for the connection recess.
Figure 18:
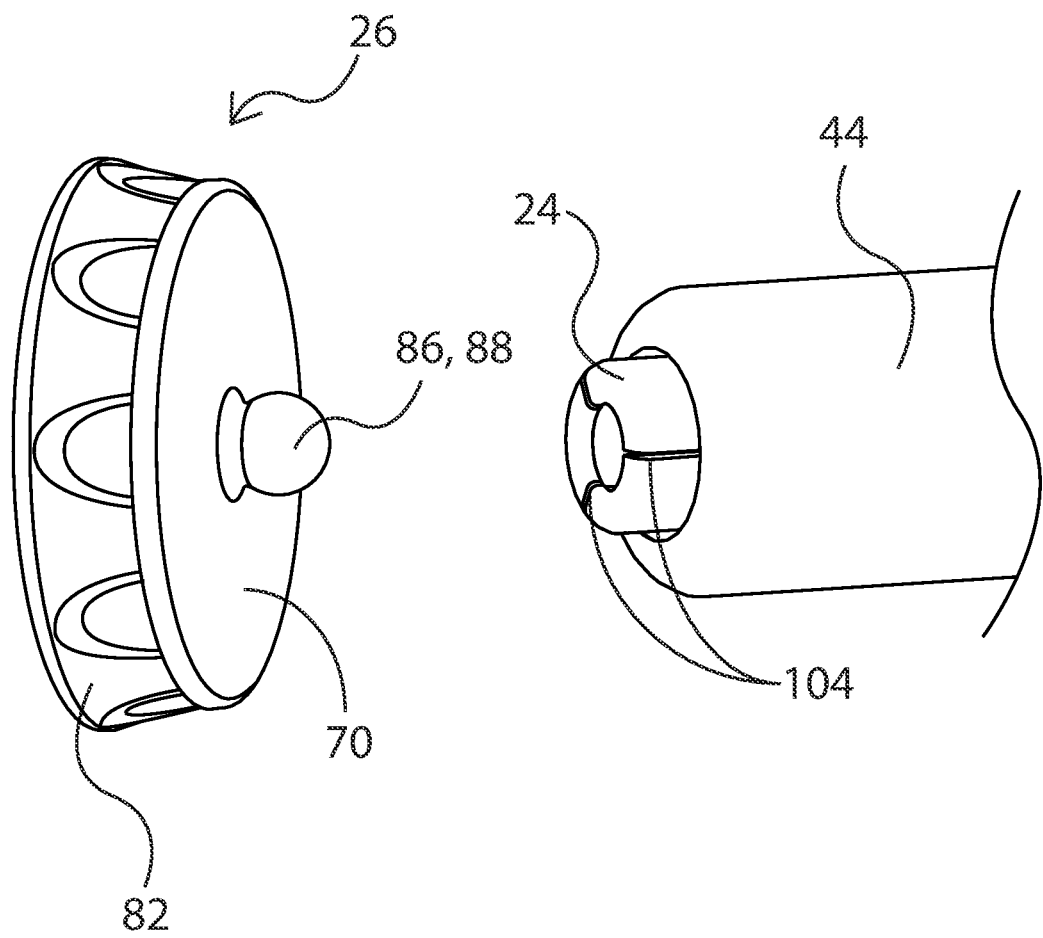
FIG. 18 is a disconnected, perspective view of the components in FIG. 16 showing the micro-needle assembly separated from the micro-channeling device.

FIGS. 16, 17a and 17b show a three-finger connection receptacle 102 whose purpose is facilitating the snap fit function. This is accomplished whereby fingers 103 temporarily spread out creating an opening of sufficiently large diameter to accept ball connector 88 into cavity and then close upon the ball connector. Fingers 103 and slots 104 near flange 89 are tailored for the flexibility of the material that pushrod 28 is made of to provide the best snap fit design, the longer the fingers, the more flexibility. The hemispherical shape on the base of the cavity of connection receptacle 102 provides additional material where fingers 103 meet the base to reinforce and disburse stress at the pushrod's 28 greatest potential breakage points. These breakage points endure the greatest stress from lateral thrusts introduced in small measure when attaching/detaching the needle assembly and are introduced in larger measure in the event of an operator accidentally dropping the micro-channeling device 22. Fewer numbers of fingers also adds more material to each individual finger's stress relief. Generally fiver fingers or less is preferable and it has been found that three fingers are optimal.

In practice, needle tip connector 24 serves to hold micro-needle assembly 26 substantially perpendicular to the reciprocating motion. However, ball connector 88 also allows for micro-needling assembly 26 to rotate and align needle side 92 parallel to the skin surface. This enables the needles to penetrate perpendicularly to the skin surface and thereby minimizes the possibility of potential damage such as skin tares, which can give rise to excess inflammation and increasing recovery time. Ball connector 88 provides from 0-degrees to a maximum of 45-degrees of angular rotation in both axes perpendicular to the reciprocation axis. There also exists a gap 87 between device connection side 72 of mounting plate 70 and fingers 103 of pushrod 28. Gap 87 allows for rotation of micro-needle assembly 26 relative to pushrod 28 to occur and may also be used to limit the maximum rotation allowed.

The micro-needling system 20 described in this disclosure provides several advantages over prior art devices. The system provides for a snap fit connection that allows for easy interchange of micro-needling assemblies 26. The ball connector 88 allows for rotation of the micro-needling assemblies to the contour angles of the skin being treated. The thinness of the disc allows for ease of treatment in skin grooves and creases. The disc-shaped flat base prevents needles from unintentionally going deeper into the skin no matter how much force is applied during treatment. The large diameter of micro-needling assembly 26 allows for allows for much faster treatment times. The large diameter of the micro-needling assembly allows for the use of a "tapping" motion, rather than the "dragging" motion that can lead to scratching. The present system also eliminates any possibility of "backflow contamination" of the micro-channeling device 22.

While several embodiments of the invention, together with modifications thereof, have been described in detail herein and illustrated in the accompanying drawings, it will be evident that various further modifications are possible without departing from the scope of the invention. The scope of the claims should not be limited by the preferred embodiments set forth in the examples, but should be given the broadest interpretation consistent with the description as a whole.

What is claimed is:

1. A micro-needle array assembly; comprising:
   a) a disc-shaped needle mounting plate, the disc-shaped needle mounting plate having a thickness;
   b) an array of needles passing through the thickness of the disc-shaped needle mounting plate;
   c) a disc-shaped attachment plate having a connection side and a needle side, a ball connector projecting perpendicularly from the connection side, the disc-shaped needle mounting plate integrated at the needle side so that the array of needles emanate away from the ball connector; and
   d) a disc-shaped safety cap for covering the needles, the disc-shaped safety cap has an outer perimeter, the disc-shaped safety cap has a grip enhancing pattern along the outer perimeter for ergonomic grip in removing the safety cap.

2. The micro-needle array assembly as recited in claim 1, wherein the disc-shaped safety cap includes an air hole.

3. The micro-needle array assembly as recited in claim 1, wherein the array of needles are embedded within a disc-shaped needle mounting plate.

4. The micro-needle array assembly as recited in claim 3, wherein the disc-shaped needle mounting plate and disc-shaped attachment plate fit together by a press fit seal.

5. The micro-needle array assembly as recited in claim 3, wherein when the disc-shaped attachment plate and disc-shaped needle mounting plate are combined they have a disc thickness that is less than 0.5-centimeter.

6. The micro-needle array assembly as recited in claim 1, wherein the array of needles have two or more lengths.

7. The micro-needle array assembly as recited in claim 1, wherein each needle is coated with at least one coating from the group including titanium nitride and diamond like carbon.

8. The micro-needle array assembly as recited in claim 1, wherein the disc-shaped attachment plate includes a mounting plate recess with an interior lip for accepting disc-shaped needle mounting plate.

9. A micro-needle array assembly; comprising:
   a) a disc-shaped needle mounting plate, the disc-shaped needle mounting plate having a thickness;
   b) an array of needles passing through the thickness of the disc-shaped needle mounting plate;
   c) a disc-shaped attachment plate having a connection side and a needle side, a ball connector projecting perpendicularly from the connection side, the disc-shaped needle mounting plate integrated at the needle side so that the array of needles emanate away from the ball connector; and
   d) a disc-shaped safety cap for covering the needles, the disc-shaped safety cap having a snap fit to secure the disc-shaped safety cap directly to the disc-shaped needle mounting plate.

\* \* \* \* \*